(12) United States Patent
Hsiao

(10) Patent No.: US 11,338,155 B2
(45) Date of Patent: May 24, 2022

(54) RADIATION IRRADIATION SYSTEM AND POSITIONING ASSEMBLY FOR RADIATION IRRADIATION SYSTEM

(71) Applicant: NEUBORON MEDTECH LTD., Jiangsu (CN)

(72) Inventor: Ming-chen Hsiao, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 176 days.

(21) Appl. No.: 16/412,792

(22) Filed: May 15, 2019

(65) Prior Publication Data

US 2019/0275349 A1 Sep. 12, 2019

Related U.S. Application Data

(63) Continuation of application No. PCT/CN2017/092731, filed on Jul. 13, 2017.

(30) Foreign Application Priority Data

Mar. 29, 2017 (CN) .......................... 201710195539.0
Mar. 29, 2017 (CN) .......................... 201720314710.0

(51) Int. Cl.
*A61N 5/10* (2006.01)
*A61B 90/18* (2016.01)
(Continued)

(52) U.S. Cl.
CPC .............. *A61N 5/103* (2013.01); *A61B 90/18* (2016.02); *A61G 13/1275* (2013.01);
(Continued)

(58) Field of Classification Search
CPC . A61N 5/103; A61N 5/1049; A61N 2005/109
See application file for complete search history.

(56) References Cited

U.S. PATENT DOCUMENTS 3,762,404 A   10/1973  Sakita
6,027,777 A * 2/2000  Hirano ..................... A47G 9/10
                                                    428/137
(Continued)

FOREIGN PATENT DOCUMENTS

CN      202802547 U     3/2013
CN      105396228 A     3/2016
(Continued)

OTHER PUBLICATIONS

International Search Report of PCT/CN2017092731, dated Oct. 14, 2019.
(Continued)

*Primary Examiner* — David P Porta
*Assistant Examiner* — Djura Malevic
(74) *Attorney, Agent, or Firm* — Locke Lord LLP; Tim Tingkang Xia, Esq.

(57) ABSTRACT

The present disclosure provides a positioning assembly for a radiation irradiation system. The positioning assembly includes a shielding body made of polymer and radiation shielding material capable of shielding the radiation and a sealing bag for accommodating the shielding body, when the target to be irradiated is placed on the positioning assembly, the positioning assembly is recessed with a shape of the target at the position where the target is placed and forms a contour corresponding to the target to position the target to be irradiated.

20 Claims, 3 Drawing Sheets

(51) Int. Cl.
  *A61G 13/12* (2006.01)
  *G21F 3/00* (2006.01)
  *G21F 1/02* (2006.01)
  *A61B 90/00* (2016.01)
  *A61B 90/10* (2016.01)

(52) U.S. Cl.
  CPC ......... *A61N 5/1049* (2013.01); *A61N 5/1077* (2013.01); *G21F 1/02* (2013.01); *G21F 3/00* (2013.01); *A61B 2090/0445* (2016.02); *A61B 2090/101* (2016.02); *A61N 2005/109* (2013.01); *A61N 2005/1094* (2013.01)

(56) References Cited

U.S. PATENT DOCUMENTS

| | | |
|---|---|---|
| 2015/0143633 A1 | 5/2015 | Kraus et al. |
| 2015/0327941 A1 | 11/2015 | Haynes |
| 2016/0158578 A1* | 6/2016 | Liu .................. G21K 1/10 600/1 |
| 2016/0158579 A1 | 6/2016 | Liu et al. |
| 2016/0213337 A1 | 7/2016 | Coppens et al. |

FOREIGN PATENT DOCUMENTS

| | | |
|---|---|---|
| CN | 105611968 A | 5/2016 |
| CN | 205339881 U | 6/2016 |
| CN | 106264585 A | 1/2017 |
| CN | 106415732 A | 2/2017 |
| DE | 19706554 A1 | 4/1998 |
| EP | 2645936 A1 | 10/2013 |
| EP | 2874473 A1 | 5/2015 |
| EP | 3527261 A1 | 8/2019 |
| JP | 2002153457 A | 5/2002 |
| JP | 2004233168 A | 8/2004 |
| JP | 2008125650 A | 6/2008 |
| JP | 201432168 | 2/2014 |
| JP | 2014055854 A | 3/2014 |
| JP | 2015231497 A | 12/2015 |
| WO | 2009057328 A1 | 5/2009 |
| WO | 2012121765 A1 | 9/2012 |
| WO | 2013057588 A2 | 4/2013 |

OTHER PUBLICATIONS

International Search Report of PCT/CN2017/092731, dated Sep. 27, 2017.

* cited by examiner

RADIATION IRRADIATION SYSTEM AND POSITIONING ASSEMBLY FOR RADIATION IRRADIATION SYSTEM

RELATED APPLICATION INFORMATION

This application is a continuation of International Application No. PCT/CN2017/092731, filed on Jul. 13, 2017, which claims priority to Chinese Patent Application No. 201710195539.0, and Application No. 201720314710.0, filed on Mar. 29, 2017, the disclosures of which are hereby incorporated by reference.

FIELD OF THE DISCLOSURE

The present disclosure relates generally to a radiation irradiation system, and more particularly to a positioning assembly for a radiation irradiation system.

BACKGROUND OF THE DISCLOSURE

With the rapid development of nuclear technology-related industries, high-energy radiation rays have been widely used in many fields such as industry, medical treatment, scientific research, and etc, and the radiation safety and protection problems are becoming more and more important. The main protecting targets comprise neutrons and X-rays and gamma rays in photons.

Especially in medical field, taking neutron capture therapy for example, in which the neutron source is used to irradiate to the tumor site of the patient on the treatment bed, regardless of whether the neutron source for neutron capture therapy comes from a nuclear reactor or a nuclear reaction between charged particles from an accelerator and a neutron generator, the radiation field is a mixed radiation field, that is, the beam contains low energy to high energy neutrons, photons, especially neutrons. When radiation other than thermal neutrons is irradiated to a body, it must bring a certain degree of damage to the normal tissues of the body, and because the treatment bed is usually made of alloy such as magnesium alloy or aluminum alloy, it is easily activated for absorbing neutrons after being irradiated by radiation. Therefore, it is a great health hazard for both the patient on the treatment bed and the medical staff who come in and contact with the treatment bed after the treatment.

Therefore, it is really necessary to provide a new technical solution so as to solve the foregoing problem.

The statements in this section merely provide background information related to the present disclosure and may not constitute prior art.

SUMMARY

In order to avoid the damage to the parts not necessary to be irradiated of the target during radiation irradiation treatment, an aspect of the present disclosure provides a radiation irradiation system including a radiation irradiation device and a treatment bed for transporting a target to be irradiated to the radiation irradiation device for irradiation, the treatment bed includes a mounting table on which the target to be irradiated is placed, a supporting portion for supporting the mounting table, and a positioning assembly provided on the mounting table for positioning the target to be irradiated; the positioning assembly includes a shielding body including polymer and radiation shielding material capable of shielding the radiation and a sealing bag for accommodating the shielding body, when the target to be irradiated is placed on the positioning assembly, the positioning assembly is recessed with a shape of the target at the position where the target is placed and forms a contour corresponding to the target to position the target to be irradiated. The positioning assembly is for the target to be irradiated to be positioned, so as to improve the treatment effect for avoiding the movement of the target.

Further, in order to reuse the positioning assembly, the shielding body is made of silicone, radiation shielding material and silicone curing agent, the shielding body in the sealing bag is in a form of solid particles, after the sealing bag is vacuumed, the positioning assembly is recessed with the shape of the target to be irradiated at the position where the target is placed and forms a contour corresponding to the target to position the target to be irradiated; when the target to be irradiated on the surface of the sealing bag is removed and the sealing bag is filled with air, the positioning assembly restores to a state before being vacuumed.

It is surely feasible that the shielding body is liquid (the shielding body is without silicone curing agent), the positioning assembly is recessed with the shape of the target to be irradiated after the sealing bag is vacuumed.

Further, the radiation irradiation system is a neutron capture therapy system, the radiation irradiation device is a neutron capture therapy device, and the shielding material is neutron capture material, the neutron capture therapy device comprises a neutron generator for generating neutrons after being irradiated by a charged particle beam, a beam shaping assembly comprising a moderator and a reflector surrounding the moderator, a beam outlet, and a collimator adjacent to an outer side of the beam outlet to converge the neutrons irradiating from the beam outlet, and wherein the moderator decelerates the neutrons generated from the neutron generator to a preset energy spectrum, and the reflector leads deviated neutrons back to increase the neutron intensity within the preset energy spectrum, the neutron capture material is capable of shielding neutrons and is made of at least one of boron-containing compound or lithium-containing compound.

More particularly, the boron-containing compound or lithium-containing compound accounts for 10% to 49% by weight of the neutron capture material, and the boron-containing compound is $^{10}B_4C$ or $^{10}BN$, the lithium-containing compound is LiF or $^6LiF$, and the neutron capture material further comprises Li, C, O, Si, and Br.

In order to avoid the damage to medical staff and the target for activation of other parts of the treatment bed after being irradiated. The treatment bed is further provided with an auxiliary member between the upper surface of the mounting table and the lower surface of the positioning assembly, the auxiliary member is made of carbon fiber, and the positioning assembly is placed on the auxiliary member. The mounting table and the supporting portion are made of alloy, and the surfaces of the mounting table and the supporting portion are covered with a shielding portion which is the same material as the shielding body of the positioning assembly. The shielding portion is for preventing the activation after the alloy is irradiated by neutrons, so as to reduce the health hazard for the target or the medical staff.

In order to avoid the damage to the parts not necessary to be irradiated of the target during radiation irradiation treatment, another aspect of the present disclosure provides a radiation irradiation system including a radiation irradiation device for irradiating to a target and a positioning assembly for positioning the target, the positioning assembly includes a shielding body including polymer and radiation shielding material capable of shielding the radiation and a sealing bag for accommodating the shielding body, when the target to be irradiated is placed on the positioning assembly, the positioning assembly is recessed with a shape of the target at the position where the target is placed and forms a contour corresponding to the target to position the target to be irradiated. The positioning assembly is for the target to be irradiated to be positioned, so as to improve the treatment effect for avoiding the movement of the target.

More particularly, the polymer is silicone, the silicone is substrate of the shielding body, and the shielding body is poured into the sealing bag.

Particularly, the radiation irradiation system is a neutron capture therapy system, the shielding material is neutron capture material, the neutron capture material is made of at least one of boron-containing compound or lithium-containing compound.

Further, the boron-containing compound or lithium-containing compound accounts for 10% to 49% by weight of the neutron capture material, and the boron-containing compound is $^{10}B_4C$ or $^{10}BN$, the lithium-containing compound is LiF or $^6$LiF.

Further, the neutron capture material further comprises Li, C, O, Si, and Br.

Further, the shielding body is made of silicone, radiation shielding material and silicone curing agent, and the shielding body in the sealing bag is in a form of solid particles.

Further, the solid particulate form refers to solids with maximum diameters between 0.01 mm and 10 mm.

Further, the sealing bag is provided with a sealing port for connecting to an external vacuuming device and the sealing bag is vacuumed by the vacuuming device, after the sealing bag is vacuumed, the positioning assembly is recessed with the shape of the target to be irradiated at the position where the target is placed and forms a contour corresponding to the target to position the target to be irradiated; when the target on the surface of the sealing bag is removed and the sealing bag is filled with air, the positioning assembly restores to a state before being vacuumed.

In order to avoid the damage to the parts not necessary to be irradiated of the target during radiation irradiation treatment, an aspect of the present disclosure provides a radiation irradiation system including a radiation irradiation device, a treatment bed for transporting a target to be irradiated to the radiation irradiation device for irradiation, and a positioning assembly for positioning the target to be irradiated, the positioning assembly defines a first state and a second state, when the positioning assembly is in the first state, the positioning assembly is not deformed or maintained in the first state deformed by external pressure; and when the positioning assembly is in the second state, the positioning assembly is deformed or maintained in a second state deformed by external pressure different from the first state deformed by external pressure.

Further, the positioning assembly includes a shielding body and a sealing bag for accommodating the shielding body, when the target to be irradiated is placed on the positioning assembly, the positioning assembly is deformed with the gravity of the target at the position where the target is placed, different shapes of target form different contours; when the target to be irradiated is removed from the sealing bag, the sealing bag is filled with air, the positioning assembly restores to a state before being vacuumed.

Further, the shielding body comprises polymer and radiation shielding material capable of shielding the radiation.

More particularly, the treatment bed includes a mounting table and a supporting portion, both the mounting table and the supporting portion are made of alloy.

Further, the surfaces of the mounting table and the supporting portion are covered with a shielding portion which is the same material as the shielding body of the positioning assembly.

Further, the treatment bed is further provided with an auxiliary member between the upper surface of the mounting table and the lower surface of the positioning assembly, the auxiliary member is made of carbon fiber, and the positioning assembly is placed on the auxiliary member.

In the disclosure, the first state defines two situations, one situation is that the positioning assembly is not under external pressure and is not deformed, another situation is that the positioning assembly is deformed under external pressure (which refers to the first deformed state); the second state defines two situations, one situation is that the positioning assembly is deformed with external pressure (which can be understood that the situation is the same as the first deformed state), another situation is that the positioning assembly is under external pressure and deformed to a second deformed state different from the first deformed state.

Compared to the prior art, the radiation irradiation system of the present disclosure provides a positioning assembly for positioning the target to improve the treatment effect for avoiding the movement of the target. And the shielding effect of the positioning assembly avoids the damage to the parts not necessary to be irradiated of the target during radiation irradiation treatment.

Further areas of applicability will become apparent from the description provided herein. It should be understood that the description and specific examples are intended for purposes of illustration only and are not intended to limit the scope of the present disclosure.

DETAILED DESCRIPTION

The following description of the preferred embodiments is merely exemplary in nature and is in no way intended to limit the invention, its application, or uses.

With the rapid development of nuclear technology-related industries, radiation has been widely used in many fields such as industry, medical treatment, scientific research, and etc, and the radiation safety and protection problems are becoming more and more important, especially in medical field, taking neutron capture therapy for example, it has been increasingly used as an effective treatment for cancer in recent years, with boron neutron capture therapy being the most common, and neutrons for boron neutron capture therapy can be supplied by nuclear reactors or accelerators.

Regardless of whether the neutron source for neutron capture therapy comes from a nuclear reactor or a nuclear reaction between charged particles from an accelerator and a neutron generator, the radiation field is a mixed radiation field, that is, the beam contains low energy to high energy neutrons, and photons. In boron neutron capture therapy for deep tumors, except for the epithermal neutrons, the greater the amount of radiations is, the greater the proportion of non-selective dose deposition on normal tissue is, so these radiations that cause unnecessary doses should be decreased. In addition, when these radiations are irradiated to a treatment bed made of alloy material such as a magnesium alloy or an aluminum alloy, the alloy material is activated. Therefore, it is a great health hazard for both the patient on the treatment bed and the medical staff who come in and contact with the treatment bed after the treatment.

Figure 1:
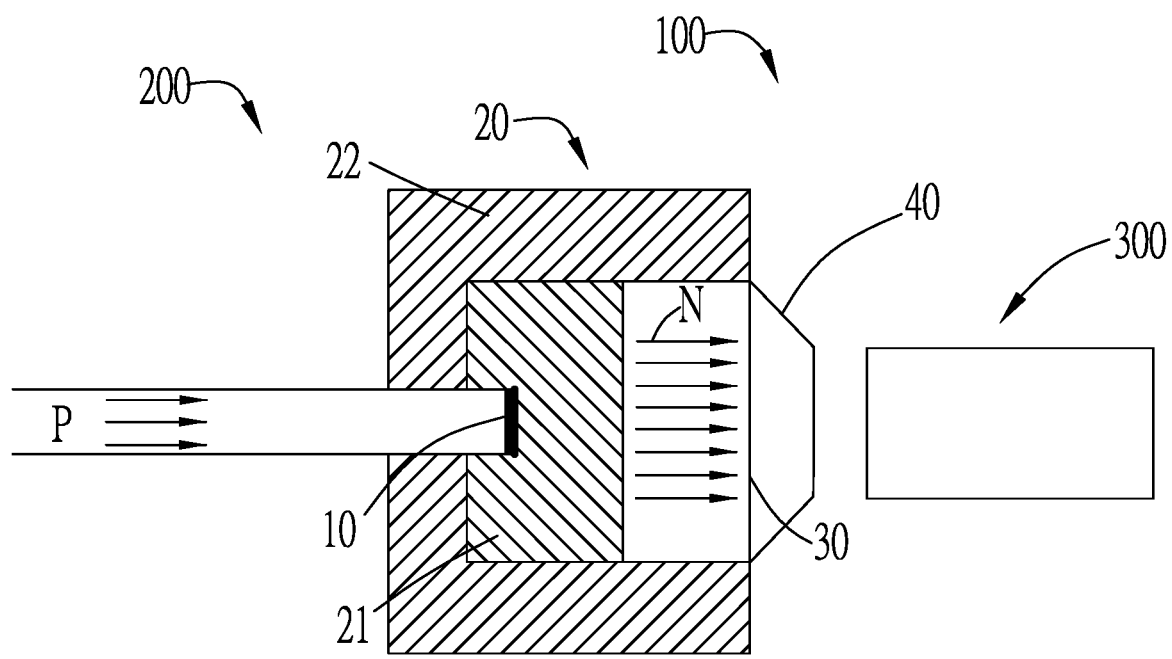
FIG. 1 is a schematic view of a neutron capture therapy system of the present disclosure.

As shown in FIG. 1, the present disclosure provides a neutron capture therapy system 100 including a neutron capture therapy device 200 and a treatment bed 300 for transporting a target to be irradiated to the radiation irradiation device for irradiation.

The neutron capture therapy device 200 includes a neutron generator 10 for generating neutrons N after being irradiated by a particle beam P, a beam shaping assembly 20 including a moderator 21 and a reflector 22 surrounding the moderator 21, a beam outlet 30, and a collimator 40 adjacent to an outer side of the beam outlet 30 to converge a neutron beam irradiating from the beam outlet 30. The moderator 21 decelerates the neutrons N generated from the neutron generator 10 to a preset energy spectrum, and the reflector 22 leads deviated neutrons back to increase the neutron intensity within the preset energy spectrum.

Figure 2:
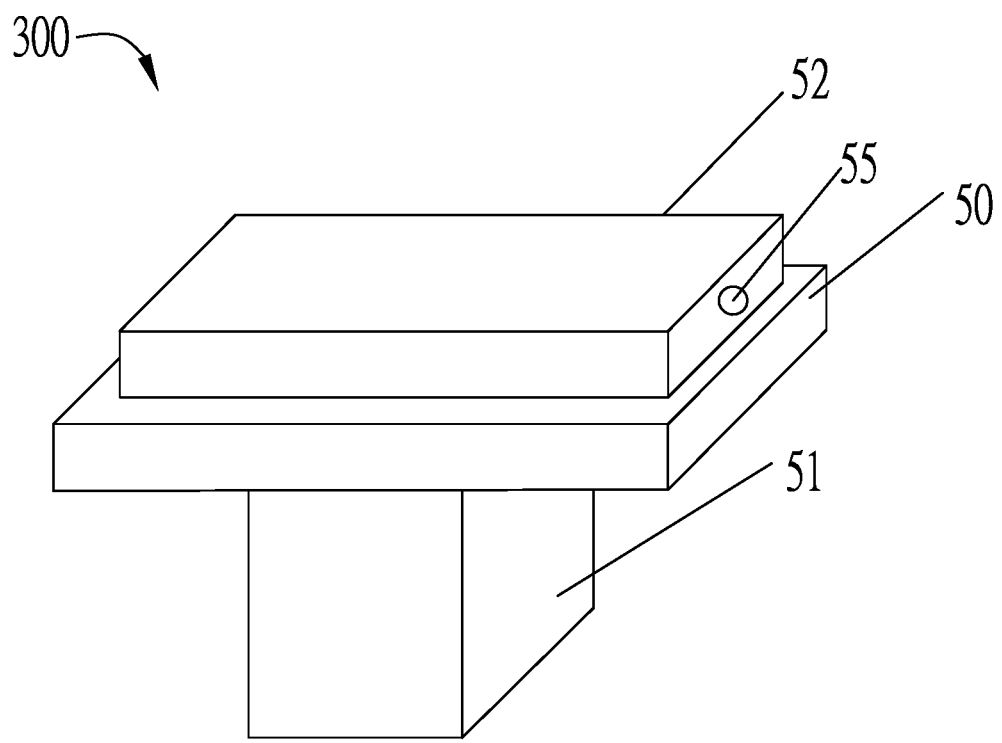
FIG. 2 is a schematic view of a treatment bed of the present disclosure.

As shown in FIG. 2, the treatment bed 300 includes a mounting table 50 on which the target to be irradiated is placed, a supporting portion 51 for supporting the mounting table 50, and a positioning assembly 52 provided on an upper surface of the mounting table 50 for positioning the target to be irradiated.

Figure 3:
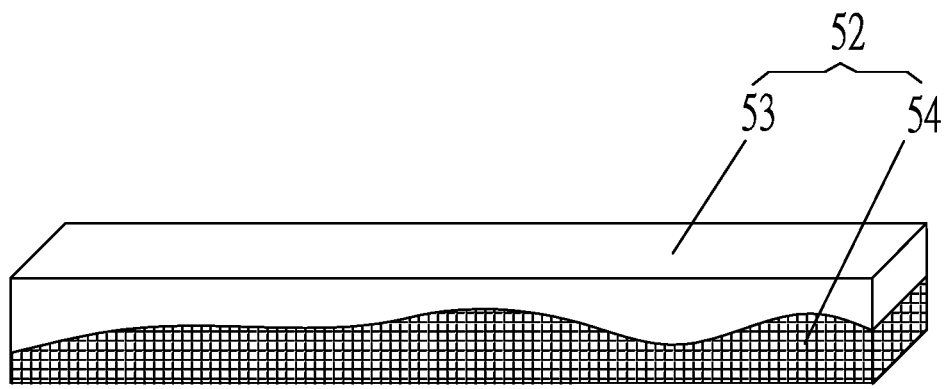
FIG. 3 is cross-sectional view of the positioning assembly of the present disclosure.

Referring to FIG. 3, the positioning assembly 52 includes a sealing bag 53 and a shielding body 54 accommodated in the sealing bag 53, and the shielding body 54 is made of silicone, neutron capture material, and silicone curing agent. The silicone can also be replaced by other polymers, and the silicone in the shielding body 54 is used as substrate. Certainly, the silicone may be replaced by other polymer, and the detailed descriptions are not provided herein again. The neutron capture material is made of at least one of boron-containing compound or lithium-containing compound, and the boron-containing compound or lithium-containing compound accounts for 10% to 50% by weight of the neutron capture material. In this embodiment, the selected neutron capture material is $^{10}BN$, and the neutron capture material further includes Li, C, O, Si, and Br.

The shielding body 54 in the sealing bag 53 is in a form of solid particles, and the sealing bag 53 is provided with a sealing port 55 for connecting to an external vacuuming device (not shown). When the target to be irradiated is placed in the positioning assembly 52, the solid particulate shielding body 54 in the sealing bag 53 is recessed with the gravity of the target and forms a shape the same as the contour of the target. The sealing bag 53 is vacuumed by using the vacuuming device (not shown), and the shape of the recessed portion of the positioning assembly 52 that is the same as the contour of the target is able to position the target to be irradiated. When the sealing bag 53 is no longer in a vacuumed state, the positioning assembly 52 restores to a state before the target is placed on the positioning assembly 52. It can be seen that the positioning assembly 52 described in the present disclosure can be reused and can be applied to targets in different body types.

In the present disclosure, the solid particulate form refers to solids with maximum diameters between 0.01 mm and 10 mm.

Certainly, the shielding body can be made directly from the silicone and the neutron capture material, in which case the shielding body is in a flowable liquid form having a certain viscosity. The flowable shielding body is poured into the sealing bag 53. When the target to be irradiated is placed on the positioning assembly 52, the shielding body in flowable state in the sealing bag 53 is recessed with the gravity of the target and forms a shape the same as the contour of the target. The sealing bag 53 is vacuumed by using the vacuuming device (not shown), and the shape of the recessed portion of the positioning assembly 52 that is the same as the contour of the target is able to position the target to be irradiated.

Figure 4:
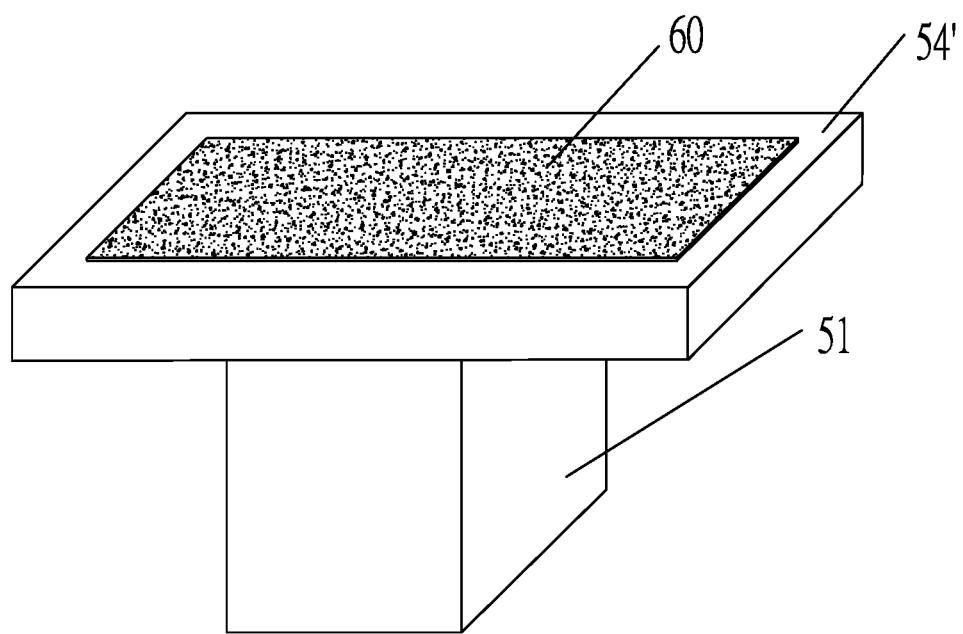
FIG. 4 is a schematic view of the mounting table and the supporting member of the present disclosure.

Referring to FIG. 4, in the present disclosure, both the mounting table 50 and the supporting portion 51 are made of alloy material, and the surfaces of the mounting table 50 and the supporting portion 51 are covered with a shielding portion 54' capable of preventing activation of the mounting table 50 and the supporting portion 51 after being irradiated with a neutron beam. The shielding portion 54' herein is the same material as the solid particulate shielding body 54 in the sealing bag 53 of the positioning assembly 52 described above. That is, the shielding portion 54' which is coated on the surface of the mounting table 50 and the supporting portion 51 is substantially the same as the shielding body 54 in the sealing bag 53, and is merely different in appearance. The thickness of shielding portion 54' coated on the surface of the mounting table 50 and the supporting portion 51 is not less than 1 cm.

The treatment bed 300 is also provided with an auxiliary member 60 between the upper surface of the mounting table 50 and the lower surface of the positioning assembly 52. The auxiliary member 60 is made of carbon fiber, and the positioning assembly 52 is placed on the auxiliary member 60.

Figure 5:
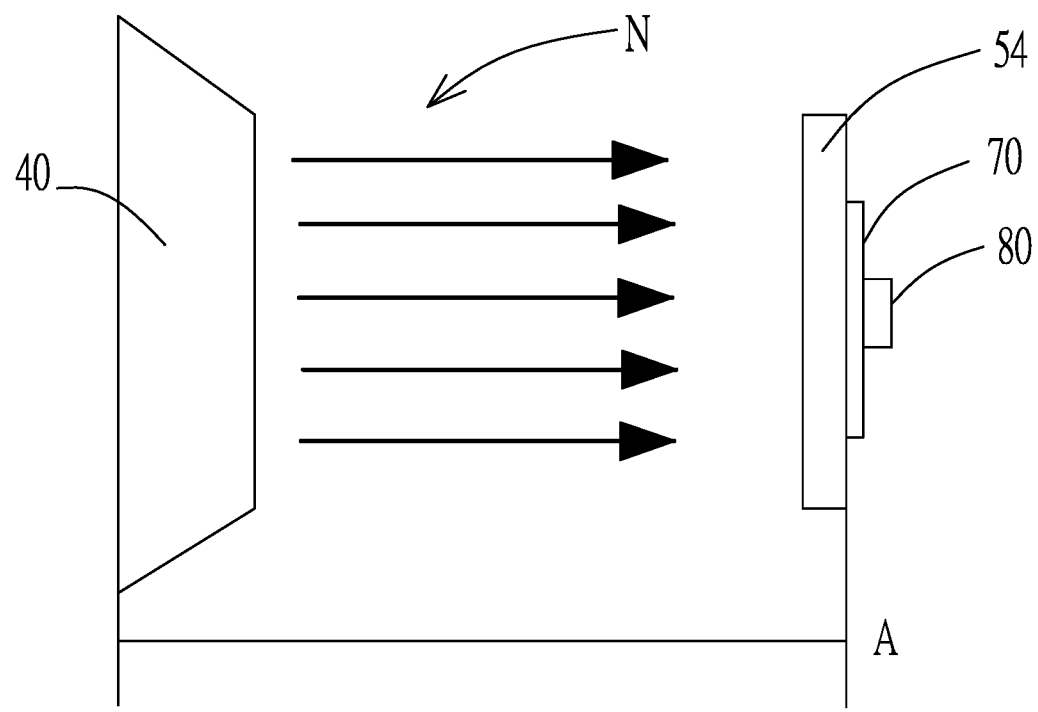
FIG. 5 is a schematic view of the present disclosure for placing a shielding body between a collimator and a metal foil to measure the neutron reaction rate.
Figure 6:
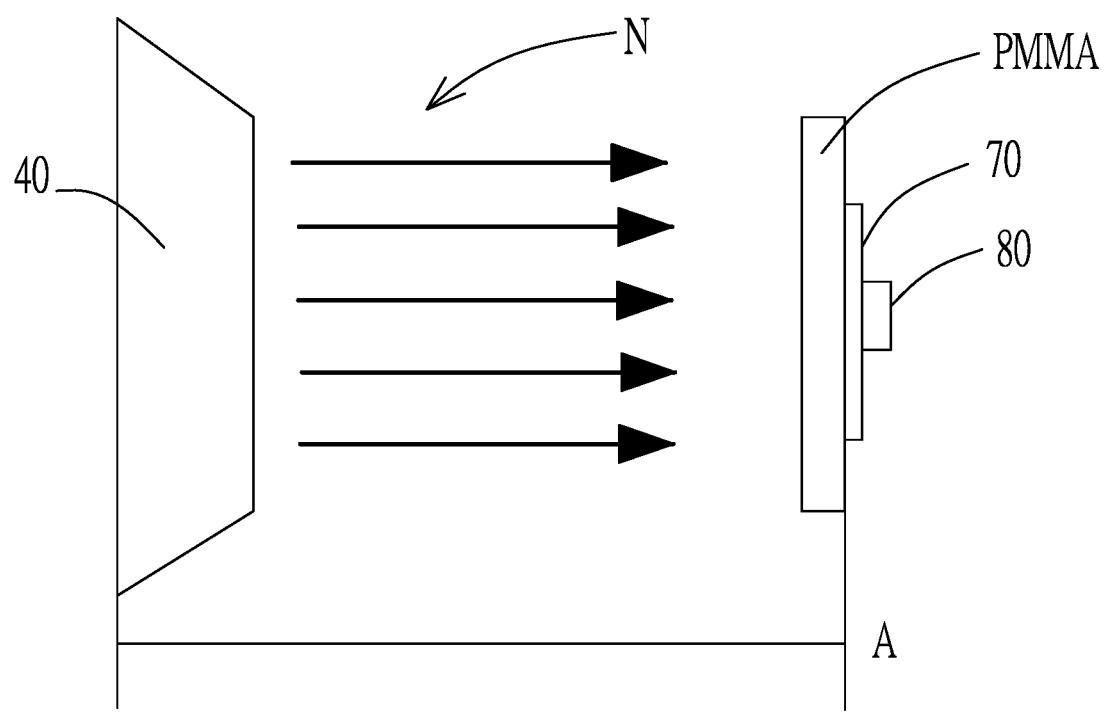
FIG. 6 is a schematic view of the present disclosure for placing PMMA between a collimator and a metal foil to measure the neutron reaction rate.

FIGS. 5 and 6 are schematic views for detecting the shielding effect of the shielding body irradiated by a neutron beam. In FIG. 5, a shielding body 54 is disposed between the collimator 40 and a metal foil 70; in FIG. 6, the shielding body 54 is replaced by PMMA (polymethyl methacrylate, which does not have any shielding effect on neutrons), and the size of the PMMA is exactly the same as the size of the shielding body 54. In the present disclosure, a metal foil 70 and a detector 80 are used to detect the neutron capture material's shielding effect against the neutron beam. Specifically, the metal foil 70 (such as a copper piece) is disposed on a surface of the shielding body 54 far away from the collimator 40 (at a position A relative to the collimator 40), and the detector 80 is connected to the metal foil 70. The neutron capture therapy device 200 irradiates to the metal foil 70 with a neutron beam, and the neutron reaction rate of the neutron beam irradiated to the metal foil 70 after being shielded by the shielding body 54 is detected by the detector 80. Similarly, the metal foil 70 is placed on the surface of the PMMA far away from the collimator 40 (at a position A relative to the collimator 40), the detector 80 is connected to the metal foil 70. The neutron capture therapy device 200 irradiates to the metal foil 70 with a neutron beam, and the neutron reaction rate of the neutron beam directly irradiated to the metal foil 70 is detected by the detector 80.

TABLE 1

Shielding effect of the shielding body on the neutron beam at different material ratios

| Neutron capture material (mass fraction per atom unit) | | | | | | |
|---|---|---|---|---|---|---|
| Li | $^{10}BN$ | C | O | Si | Br | $RR/RR_{ref}$ |
| 0.01 | 0.1 | 0.396 | 0.2185 | 0.1655 | 0.11 | 0.083 |
| 0.01 | 0.2 | 0.296 | 0.2185 | 0.1655 | 0.11 | 0.075 |
| 0.01 | 0.3 | 0.196 | 0.2185 | 0.1655 | 0.11 | 0.062 |
| 0.01 | 0.4 | 0.006 | 0.2185 | 0.1655 | 0.11 | 0.056 |
| 0.01 | 0.49 | 0.006 | 0.2185 | 0.1655 | 0.11 | 0.049 |

In Table 1, RR denotes the neutron reaction rate of a neutron beam irradiated to a metal foil (such as copper piece) after passing through the shielding body; $RR_{ref}$ is the neutron reaction rate of a neutron beam directly irradiated to a metal foil (such as copper piece). It can be seen from the ratio of RR to $RR_{ref}$ that the shielding body of the present disclosure does have a good effect on the shielding neutrons, and the smaller the ratio of RR to $RR_{ref}$ is, the better the shielding effect of the shielding body on neutrons is.

Certainly, the $^{10}BN$ content accounts for 10% to 49% by weight of the neutron capture material described in Table 1 is only a preferred embodiment. In actual manufacturing process, the content of $^{10}BN$ accounts for 10% to 100% (as shown in FIG. 7). However, when $^{10}BN$ content accounts for more than 49% by weight of the neutron capture material, the shielding ability of the shielding body on neutron beam is not greatly improved compared to the shielding ability of the shielding body accounts for 10% to 49% of $^{10}BN$ by weight. The ratio of $^{10}BN$ content by weight of the neutron capture material is preferably 10% to 49% in consideration of manufacturing cost.

It should be noted that in order to ensure the accuracy of the measurement, in the process of detecting the neutron reaction rate RR (with the shielding body 54) and $RR_{ref}$ (without the shielding body 54), the position of the metal foil 70 relative to the collimator 40 is the same.

Certainly, in the present disclosure, the neutron capture therapy system and the neutron capture material for shielding neutrons are examples for detailed description. The technical solution in the present disclosure can also be applied to other radiation irradiation systems, and the present disclosure will not describe specifically.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A radiation irradiation system comprising:
   a radiation irradiation device, wherein the radiation irradiation system is a neutron capture therapy system, the radiation irradiation device is a neutron capture therapy device including a neutron source for generating a mixed radiation field including neutrons and photons; and
   a treatment bed for transporting a target to be irradiated to the radiation irradiation device for irradiation, wherein the treatment bed comprises:
   a mounting table on which the target to be irradiated is placed;
   a supporting portion for supporting the mounting table; and
   a positioning assembly provided on the mounting table for positioning the target to be irradiated, wherein the positioning assembly is configured to be reused and comprises:
   a shielding body including polymer and radiation shielding material capable of shielding the radiation, the shielding material is neutron capture material, the neutron capture material is capable of shielding neutrons and is made of at least one of boron-containing compound or lithium-containing compound; and
   a sealing bag for accommodating the shielding body, when the target to be irradiated is placed on the positioning assembly, the positioning assembly is recessed with a shape of the target at the position where the target is placed and forms a contour corresponding to the target to position the target to be irradiated.

2. The radiation irradiation system according to claim 1, wherein the shielding body is made of silicone, radiation shielding material and silicone curing agent, the shielding body in the sealing bag is in a form of solid particles, after the sealing bag is vacuumed, the positioning assembly is recessed with the shape of the target to be irradiated at the position where the target is placed and forms a contour corresponding to the target to position the target to be irradiated; when the target to be irradiated on the surface of the sealing bag is removed and the sealing bag is filled with air, the positioning assembly restores to a state before being vacuumed.

3. The radiation irradiation system according to claim 1, wherein the neutron capture therapy device comprises a neutron generator for generating neutrons after being irradiated by a charged particle beam, a beam shaping assembly comprising a moderator and a reflector surrounding the moderator, a beam outlet, and a collimator adjacent to an outer side of the beam outlet to converge the neutrons irradiating from the beam outlet, and wherein the moderator decelerates the neutrons generated from the neutron generator to a preset energy spectrum, and the reflector leads deviated neutrons back to increase the neutron intensity within the preset energy spectrum.

4. The radiation irradiation system according to claim 3, wherein the boron-containing compound or lithium-containing compound accounts for 10% to 49% by weight of the neutron capture material, and the boron-containing compound is $^{10}B_4C$ or $^{10}BN$, the lithium-containing compound is LiF or $^6LiF$, and the neutron capture material further comprises Li, C, O, Si, and Br.

5. The radiation irradiation system according to claim 1, wherein the mounting table and the supporting portion are made of alloy, and the surfaces of the mounting table and the supporting portion are covered with a shielding portion which is the same material as the shielding body of the positioning assembly.

6. The radiation irradiation system according to claim 1, wherein the treatment bed is further provided with an auxiliary member between the upper surface of the mounting table and the lower surface of the positioning assembly, the auxiliary member is made of carbon fiber, and the positioning assembly is placed on the auxiliary member.

7. A radiation irradiation system comprising:
a radiation irradiation device for irradiating to a target; and
a positioning assembly for positioning the target, wherein the positioning assembly is configured to be reused and comprises:
a shielding body comprising polymer and radiation shielding material capable of shielding the radiation, the shielding material is neutron capture material, the neutron capture material is capable of shielding neutrons and is made of at least one of boron-containing compound or lithium-containing compound; and
a sealing bag for accommodating the shielding body,
when the target to be irradiated is placed on the positioning assembly, the positioning assembly is recessed with a shape of the target at the position where the target is placed and forms a contour corresponding to the target to position the target to be irradiated, so as to improve the treatment effect for avoiding the movement of the target.

8. The radiation irradiation system according to claim 7, wherein the polymer is silicone, the silicone is substrate of the shielding body, and the shielding body is poured into the sealing bag.

9. The radiation irradiation system according to claim 7, wherein the radiation irradiation system is a neutron capture therapy system.

10. The radiation irradiation system according to claim 9, wherein the boron-containing compound or lithium-containing compound accounts for 10% to 49% by weight of the neutron capture material, and the boron-containing compound is $^{10}B_4C$ or $^{10}BN$, the lithium-containing compound is LiF or $^6LiF$.

11. The radiation irradiation system according to claim 9, wherein the neutron capture material further comprises Li, C, 0, Si, and Br.

12. The radiation irradiation system according to claim 7, wherein the shielding body is made of silicone, radiation shielding material and silicone curing agent, and the shielding body in the sealing bag is in a form of solid particles.

13. The radiation irradiation system according to claim 12, wherein the solid particulate form refers to solids with maximum diameters between 0.01 mm and 10 mm.

14. The radiation irradiation system according to claim 7, wherein the sealing bag is provided with a sealing port for connecting to an external vacuuming device and the sealing bag is vacuumed by the vacuuming device, after the sealing bag is vacuumed, the positioning assembly is recessed with the shape of the target to be irradiated at the position where the target is placed and forms a contour corresponding to the target to position the target to be irradiated; when the target on the surface of the sealing bag is removed and the sealing bag is filled with air, the positioning assembly restores to a state before being vacuumed.

15. A radiation irradiation system comprising:
a radiation irradiation device, wherein the radiation irradiation system is a neutron capture therapy system, the radiation irradiation device is a neutron capture therapy device including a neutron source for generating a mixed radiation field including neutrons and photons, the shielding material is neutron capture material;
a treatment bed for transporting a target to be irradiated to the radiation irradiation device for irradiation; and
a positioning assembly for positioning the target to be irradiated,
wherein the positioning assembly is configured to be reused and defines a first state and a second state, when the positioning assembly is in the first state, the positioning assembly is not deformed or maintained in the first state deformed by external pressure; and when the positioning assembly is in the second state, the positioning assembly is deformed or maintained in a second state deformed by external pressure different from the first state deformed by external pressure, so as to improve the treatment effect for avoiding the movement of the target by deforming or maintaining the two different states, the positioning assembly is capable of restoring to the state before the target is placed on the positioning assembly.

16. The radiation irradiation system according to claim 15, wherein the positioning assembly comprises a shielding body and a sealing bag for accommodating the shielding body, when the target to be irradiated is placed on the positioning assembly, the positioning assembly is deformed with the gravity of the target at the position where the target is placed, different shapes of target form different contours; when the target to be irradiated is removed from the sealing bag, the sealing bag is filled with air, the positioning assembly restores to a state before being vacuumed.

17. The radiation irradiation system according to claim 16, wherein the shielding body comprises polymer and radiation shielding material capable of shielding the radiation.

18. The radiation irradiation system according to claim 15, wherein the treatment bed comprises a mounting table and a supporting portion, both the mounting table and the supporting portion are made of alloy.

19. The radiation irradiation system according to claim 18, wherein the surfaces of the mounting table and the supporting portion are covered with a shielding portion which is the same material as the shielding body of the positioning assembly.

20. The radiation irradiation system according to claim 15, wherein the treatment bed is further provided with an auxiliary member between the upper surface of the mounting table and the lower surface of the positioning assembly, the auxiliary member is made of carbon fiber, and the positioning assembly is placed on the auxiliary member.

* * * * *